US012679835B2

(12) United States Patent
Qiao et al.

(10) Patent No.: US 12,679,835 B2
(45) Date of Patent: Jul. 14, 2026

(54) BENZOTHIAZINONE DERIVATIVE SUBSTITUTED WITH TRIFLUOROMETHYL AT 6-POSITION, AND PREPARATION METHOD THEREFOR AND USE THEREOF

(71) Applicant: SOOCHOW UNIVERSITY, Suzhou (CN)

(72) Inventors: Chunhua Qiao, Suzhou (CN); Dongguang Fan, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 531 days.

(21) Appl. No.: 18/012,450

(22) PCT Filed: Mar. 29, 2021

(86) PCT No.: PCT/CN2021/083695

§ 371 (c)(1),
(2) Date: Feb. 1, 2024

(87) PCT Pub. No.: WO2022/204902

PCT Pub. Date: Oct. 6, 2022

(65) Prior Publication Data

US 2024/0254116 A1 Aug. 1, 2024

(51) Int. Cl.

| | |
|---|---|
| ***C07D 417/12*** | (2006.01) |
| ***A61K 31/5415*** | (2006.01) |
| ***A61P 31/06*** | (2006.01) |

(52) U.S. Cl.
CPC ........ *C07D 417/12* (2013.01); *A61K 31/5415* (2013.01); *A61P 31/06* (2018.01)

(58) Field of Classification Search
CPC .... C07D 417/12; A61P 31/06; A61K 31/5415
See application file for complete search history.

(56) References Cited

U.S. PATENT DOCUMENTS

2015/0353571 A1 12/2015 Miller et al.

FOREIGN PATENT DOCUMENTS

| | | |
|---|---|---|
| CN | 101809009 A | 8/2010 |
| CN | 111269197 A | 6/2020 |
| CN | 112409293 A | 2/2021 |
| CN | 113121521 A | 7/2021 |
| DE | 102014012546 A1 | 3/2016 |

*Primary Examiner* — Kamal A Saeed

(74) *Attorney, Agent, or Firm* — SZDC Law PC

(57) ABSTRACT

A benzothiazinone derivative substituted with trifluoromethyl at 6-position, and a preparation method therefor and the use thereof. A series of compounds are obtained by means of changing the benzene ring of the benzothiazinone backbone, especially by means of changing a substituent thereof. Compared with other benzothiazinone derivatives, the benzothiazinone derivative substituted with trifluoromethyl at 6-position is more stable with regard to hepatic microsomal enzymes, and has longer metabolic half-life $T_{1/2}$ and better water solubility.

7 Claims, No Drawings

BENZOTHIAZINONE DERIVATIVE SUBSTITUTED WITH TRIFLUOROMETHYL AT 6-POSITION, AND PREPARATION METHOD THEREFOR AND USE THEREOF

This application is the National Stage Application of PCT/CN2021/083695, filed on Mar. 29, 2021, which is incorporated by reference for all purposes as if fully set forth herein.

TECHNICAL FIELD

The present invention relates to the technical field of antibacterial drugs, and particularly relates to a 6-trifluoromethyl-substituted benzothiazinone derivative and a preparation method and an application thereof.

BACKGROUND OF INVENTION

Tuberculosis is one of infectious diseases. Among anti-tuberculosis drugs taking benzothiazinone (BTZ) as a skeleton and targeting at DprE1, BTZ043 (phase I) and pBTZ169 (phase II) are in the research and development stage at present, and has obvious in vitro antibacterial advantages compared with the existing clinical first-line drug Isoniazid (MIC 0.5 μM). However, the existing benzothiazinone antituberculosis drugs have poor water solubility, poor druggability and short metabolic half-life period in human liver microsomes; moreover, the failure rate of drugs in clinical evaluation phase is high and more candidate drugs are expected to be developed.

Technical Problems

The present invention creatively changes the position of the lateral chain of the benzothiazinone, especially creatively changes the piperazine ring to obtain a series of compounds, thereby achieving unexpected technical effects; importantly, compared with the benzothiazinone antituberculosis drugs in the existing research stage, the compound provided by the present invention has better water solubility, longer half-life period in human liver microsomes and better druggability.

Technical Solution

The invention adopts the following technical scheme: 6-trifluoromethyl-substituted benzothiazinone derivative and the chemical structural formula as follows:

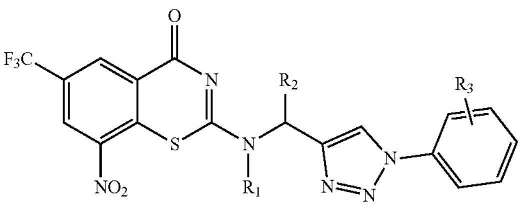

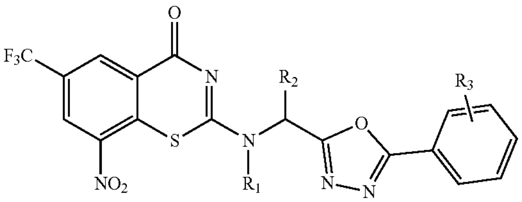

-continued

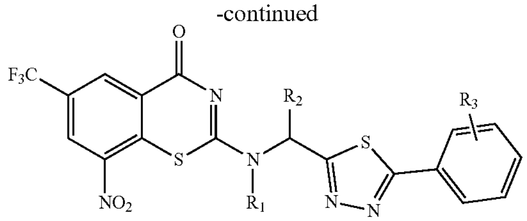

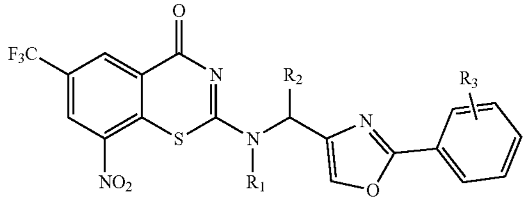

wherein: $R^1$ is hydrogen, methyl or ethyl; $R^2$ is hydrogen, methyl or ethyl; $R^3$ is halogen.

Preferably the chemical structural formula of 6-trifluoromethyl-substituted benzothiazinone derivative as follows:

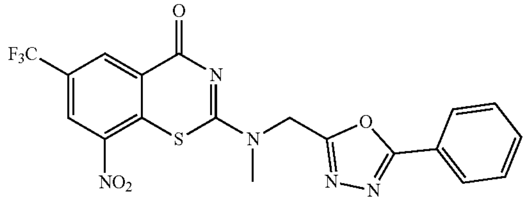

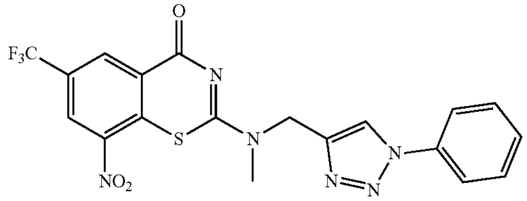

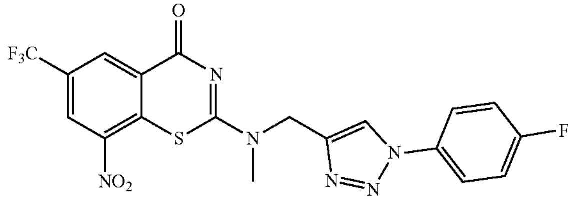

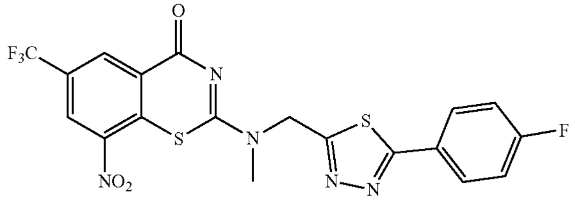

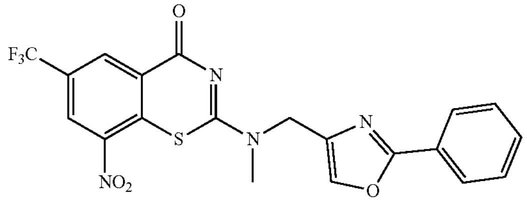

The present invention discloses the application of the 6-trifluoromethyl-substituted benzothiazinone derivative as tubercle *Bacillus* inhibitor or the application in the preparation of antituberculosis drugs.

The present invention discloses the application of a pharmaceutical composition containing the 6-trifluoromethyl-substituted benzothiazinone derivative as tubercle *Bacillus* inhibitor or the application in the preparation of antituberculosis drugs; the tuberculosis includes active tuberculosis, single-drug-resistant tuberculosis, multi-drug-resistant tuberculosis and extensive multi-drug-resistant tuberculosis; the tuberculosis includes pulmonary tuberculosis and extra-pulmonary tuberculosis; the *Bacillus* includes *Mycobacterium tuberculosis*, leprosy *Bacillus, Corynebacterium* or *Nocardia.*

The present invention discloses a pharmaceutical composition taking the 6-trifluoromethyl-substituted-benzothiazinone derivative as an active ingredient; the pharmaceutical composition is a tablet, a capsule, a granule, syrup, powder or injection; the benzothiazinone derivative of the present invention may be used as an active ingredient combined with a conventional pharmaceutical carrier to obtain a pharmaceutical composition.

The present invention discloses a preparation method of the 6-trifluoromethyl-substituted benzothiazinone derivative as follows: reacting the compound A5 with an azide to obtain a 6-trifluoromethyl-substituted-benzothiazinone derivative; or reacting the compound A4 with a compound BC to obtain 6-trifluoromethyl-substituted-benzothiazinone derivative; or reacting the compound A4 with a compound D2 to obtain a 6-trifluoromethyl-substituted-benzothiazinone derivative.

Wherein the chemical structural formula of compound A5 as follows:

A5

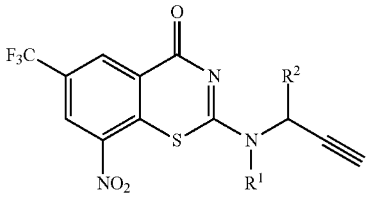

the chemical structural formula of the azide as follows:

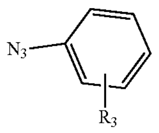

the chemical structural formula of compound A4 as follows:

A4

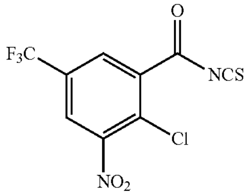

the chemical structural formula of compound BC as follows:

BC

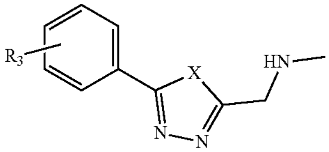

the chemical structural formula of compound D2 as follows:

D2

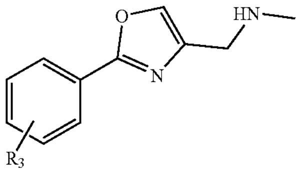

$R^1$ is hydrogen, methyl or ethyl; $R^2$ is hydrogen, methyl or ethyl; $R^3$ is hydrogen or halogen; X is O or S.

Further, the reaction of the compound A5 and the azide compound was carried out at room temperature in the presence of copper salt, a reducing agent and inorganic base; the reaction of compound A4 with compound BC was carried out at room temperature; the reaction of compound A4 with compound D2 was carried out at room temperature. A compound A1 was used as a starting material to react with oxalyl chloride after nitration, and reacts with ammonium thiocyanate to generate a compound A4.

The chemical structural formula of compound A1 as follows:

A1

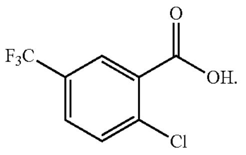

Specifically, the route of the preparation method of the 6-trifluoromethyl-substituted benzothiazinone derivative:

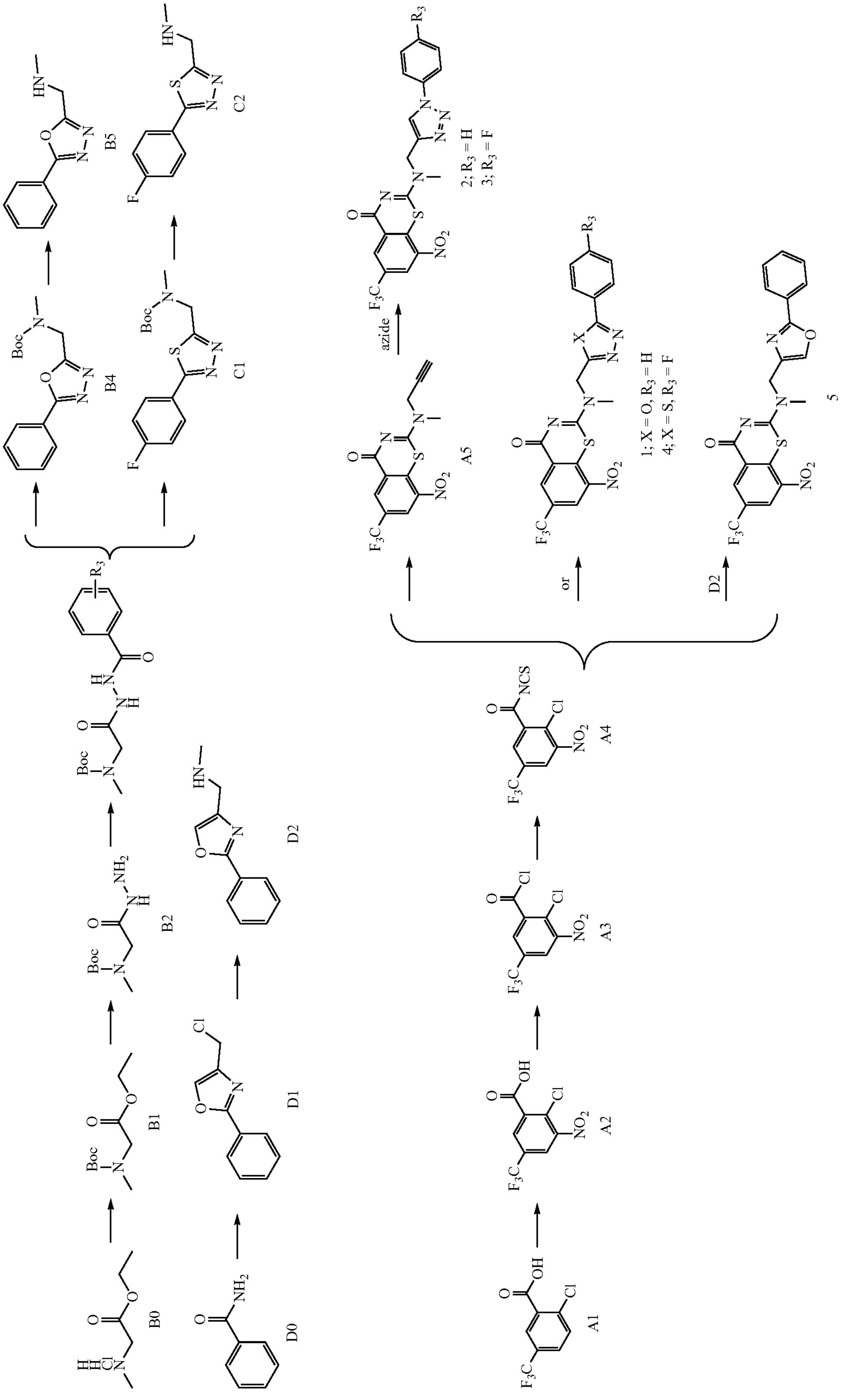
B0 B1 B2 B4 B5 C1 C2 D0 D1 D2 A1 A2 A3 A4 A5
2; $R_3$ = H
3; $R_3$ = F
1; X = O, $R_3$ = H
4; X = S, $R_3$ = F
5

The preparation method is as follows:

the step of B0→B3 is: sarcosine ethyl hydrochloride B0 was protected by Boc acid anhydride and converted into N-Boc intermediate B1. Secondly, the intermediate B1 was subjected to hydrazinolysis to obtain a hydrazide intermediate B2, which was subjected to condensation reaction with various aryl carboxylic acids under the condition that carbonyl diimidazole was used as a condensation reagent to obtain various dihydrazide intermediates B3 and derivatives thereof.

The step of →B5 is: the intermediate B3 was subjected to a dehydration reaction to prepare oxadiazole ring intermediate B4. Subsequently, the intermediate B4 was subjected to de-Boc under the action of trifluoroacetic acid to obtain a compound B5 and derivatives thereof.

The step of →C2 is: under the action of Lawesson reagent, compound B3 underwent intramolecular cyclization reaction to produce the intermediate C1 and derivatives thereof, and the protecting group Boc was removed under the action of trifluoroacetic acid to produce side chain amine C2 and derivatives thereof.

The step of →D2 is: benzamide DO and its derivatives reacted with 1, 3-dichloroacetone to generate oxazole ring intermediate D1 and its derivatives, then D1 and methylamine generated nucleophilic substitution to generate amine D2 and derivatives thereof.

The step of →A5 is: a compound A1 was used as a starting material and underwent nitration to obtain the 3-nitration product A2. The intermediate A2 reacted with oxalyl chloride to convert the carboxyl group to acyl chloride A3, which further reacted with ammonium thiocyanate to form thiocyanate intermediate A4. Finally, A4 underwent a cyclization reaction with N-methylpropargylamine, resulting in the cyclization product A5.

The compound A5 and azidobenzene or p-fluoro azidobenzene had click reaction to obtain the products 2 and 3 of the present invention. A4 underwent intramolecular cyclization reactions with various amines B5, D2, C2 and their derivatives to obtain products 1, 4, 5 and their derivatives of the present invention.

BENEFICIAL EFFECTS

The invention discloses a series of compounds with innovative structures, and the results of the Examples showed that the 6-trifluoromethyl substituted benzothiazinone derivative of the invention showed obvious bacteriostatic effect, which was much better than that of Isoniazid of the positive control (the existing clinical drug), and particularly the invention solved the defects of low water solubility and short metabolic half-life period in human liver microsomes of the existing bacteriostatic agent.

EXAMPLES OF THE PRESENT INVENTION

The following is an explanation of the method of the present invention through specific Examples, but the present invention is not limited to this. The experimental procedures described in the Examples are conventional unless otherwise specified, and the testing methods of the minimal inhibitory concentration MIC (ng/mL) of the involved compounds against *Mycobacterium tuberculosis* (H37 Rv, standard tuberculosis strain), metabolic half-life period in human liver microsomes ($T_{1/2}$, min) and solubility (g/mL) are the existing methods; the reagents and materials may be prepared or obtained commercially or by conventional methods, unless otherwise specified.

Example 1: Compound 1:2-(methyl ((5-phenyl-1, 3, 4-oxadiazol-2-yl) methyl) amino)-8-nitro-6-(trifluoromethyl)-4H-benzo [e] [1,3] Thiazin-4-ketone

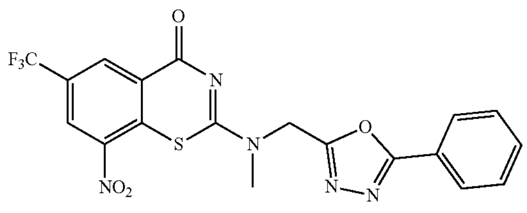 [SMILES: CN(Cc1nnc(-c2ccccc2)o1)c1nc(=O)c2cc(C(F)(F)F)cc([N+](=O)[O-])c2s1]

Sarcosine hydrochloride (500 mg, 3.26 mmol) was dissolved in DMF (20 mL), and triethylamine (362 mg, 3.58 mmol) was added on the basis of stirring, and $Boc_2O$ (853 mg, 3.90 mmol) was added under ice bath. Stirring was then continued at room temperature, monitored by TLC plates, and the reaction was completed after 12 h. The reaction system was poured into water, extracted with ethyl acetate (100 mL×3), the organic phase was washed with brine, dried with anhydrous sodium sulfate, filtered to remove the drying agent, concentrated, and subjected to column chromatography (PE:EA=5:1) to obtain compound B1 (500 mg, yield: 71%) as a colorless oily compound.

The compound B1 (500 mg, 2.30 mmol) was dissolved in ethanol (10 mL) and hydrazine hydrate (2 mL) was added on the basis of stirring. Stirring was then continued at room temperature, monitored by TLC plates, and the reaction was completed after 4 h. The reaction system was concentrated, and purified by column chromatography (DCM:MeOH=20:1) to obtain the compound B2 (400 mg, yield: 86%).

Benzoic acid (100 mg, 0.82 mmol) was dissolved in acetonitrile, and N, N'-Carbonyldiimidazole (CDI) (146 mg, 0.90 mmol) was added, the temperature was raised to 45° C., the system was stirred at this temperature for 45 min, the compound B2 (166 mg, 0.82 mmol) was added, the system was cooled to room temperature and stirring continued, monitored by TLC plates, and the reaction was completed after 13 h. The reaction system was poured into 2M citric acid aqueous solution (10 mL), extracted with ethyl acetate (100 mL×3), dried with anhydrous sodium sulfate, filtered to remove the drying agent, concentrated under reduced pressure, and subjected to column chromatography (PE:EA=1:1) to obtain the compound B3 (200 mg, yield: 80%) as a white solid compound. $^1H$ NMR (400 MHz, DMSO-$d_6$) δ 10.38 (d, J=11.5 Hz, 1H), 9.99 (d, J=15.6 Hz, 1H), 7.88 (d, J=7.2 Hz, 2H), 7.57 (t, J=6.9 Hz, 1H), 7.49 (t, J=7.0 Hz, 2H), 3.93-3.91 (m, 2H), 2.86-2.83 (m, 3H), 1.41-1.39 (m, 9H).

The compound B3 (200 mg, 0.65 mmol) was dissolved in Dichloromethane (DCM), and imidazole (89 mg, 1.30 mmol), triphenylphosphine (341 mg, 1.30 mmol) and carbon tetrabromide (432 mg, 1.30 mmol) were added sequentially. Stirring was then continued at room temperature, monitored by TLC plates, and the reaction was completed after 8 h. The system was concentrated and subjected to column chromatography (PE:EA=2:1) to obtain the B4 (150 mg, yield: 75%) as a colorless oily substance. $^1H$ NMR (400 MHz, DMSO-$d_6$) δ 7.97 (d, J=6.5 Hz, 2H), 7.65-7.60 (m, 3H), 4.71 (s, 2H), 2.94 (s, 3H), 1.42-1.34 (m, 9H).

The compound B4 (150 mg, 0.52 mmol) was dissolved in DCM (10 mL) and trifluoroacetic acid (4 mL) was added under ice bath. Stirring was then continued at room temperature, monitored by TLC plates, and the reaction was completed after 3 h. The mixture was adjusted to pH=9 with a saturated potassium carbonate solution, extracted with ethyl acetate (50 mL×3), dried with anhydrous sodium sulfate, filtered to remove the drying agent, and concentrated to obtain the B5 (80 mg, yield: 89%) as a colorless oily substance. $^1H$ NMR (400 MHz, DMSO-$d_6$) δ 7.99 (d, J=6.7 Hz, 2H), 7.61-7.59 (m, 3H), 3.94 (s, 2H), 2.33 (s, 3H).

The compound 2-chloro-5-(trifluoromethyl) benzoic acid A1 (1.0 g, 4.45 mmol) was dissolved in 50 mL of concentrated sulfuric acid, and then the potassium nitrate (900 mg, 8.91 mmol) was added at 0° C. Stirring was then continued at 90° C., monitored by TLC plates, and the reaction was completed after 3 h. The reaction system was cooled to room temperature, poured into ice water, and a large amount of white solid precipitated, filtered, and washed three times with ice water to obtain the compound A2 (1.1 g, yield: 91%) as a white solid. $R_f$=0.2, dichloromethane/methanol=50:1; the compound A2 (50 mg, 0.18 mmol) was dissolved with stirring in 10 mL of redistilled dichloromethane, followed by the addition of oxalyl chloride (92 mg, 0.72 mmol) and catalytic equivalent of DMF and reaction at room temperature, monitored by TLC plates and the reaction was completed after 1 h. The solvent was spin-dried to obtain the intermediate of acyl chloride directly for the next reaction. The previous compound (acyl chloride intermediate) was dissolved in dry DCM (10 mL) under nitrogen followed by the addition of 2 drops of polyethylene glycol and the anhydrous acetone solution of ammonium thiocyanate (21 mg, 0.27 mmol) was added dropwise to the solution for reaction at room temperature, monitored by TLC plates for 20 minutes to obtain the intermediate compound A4. It was directly used for the next step of the reaction without purification. To the reaction system of the above compound was added side-chain amine compound B5 (41 mg, 0.21 mmol), and the cyclization reaction was carried out at room temperature, and the reaction was monitored by TLC plates till completion. The reaction mixture was concentrated under reduced pressure, and the residue was diluted with water (30 mL) and extracted with dichloromethane (50 mL×3), dried with anhydrous sodium sulfate, filtered, concentrated, and subjected to column chromatography (PE:EA=1:1) to obtain the yellow solid compound 1 (50 mg, yield: 59%). $^1H$ NMR (400 MHz, $CDCl_3$) δ 9.14 (s, 1H), 8.81 (s, 1H), 8.02 (d, J=7.6 Hz, 2H), 7.56-7.47 (m, 3H), 5.42 (s, 2H), 3.55 (s, 3H). $^{13}C$ NMR (151 MHz, $CDCl_3$) δ 166.1, 166.1, 164.9, 160.9, 144.1, 133.9 (d, J=2.8 Hz), 132.3, 130.3 (q, J=35.5 Hz), 129.3, 127.2, 126.6, 126.3 (d, J=3.2 Hz), 122.4 (q, J=274.0 Hz), 45.2, 36.7. HRMS (+ESI) m z calcd for $C_{19}H_{13}F_3N_5O_4S^+$ $[M+H]^+$=464.0635 found 464.0632.

Example 2: Compound 2:2-(1-phenyl ((1-1H-1,2,3-triazole-4-yl) methyl) (methyl) amino)-8-nitro-6-(trifluoromethyl)-4H-benzo [e] [1,3] Thiazin-4-ketone

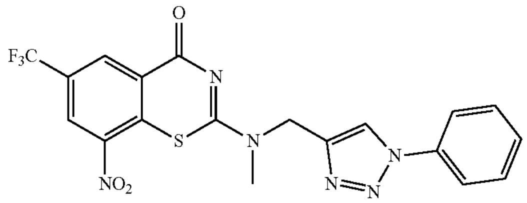 [SMILES: CN(Cc1cn(-c2ccccc2)nn1)c1nc(=O)c2cc(C(F)(F)F)cc([N+](=O)[O-])c2s1]

The synthesis of compound A5 was carried out by using the compound A4 (400 mg, 1.48 mmol) and N-methylpropargylamine (113 mg, 1.63 mmol) through the cyclization reaction step in Example 1, column chromatography (dichloromethane:methanol=200:1) to obtain compound A5 (40 mg, yield: 44%) as a yellow solid; $R_f$=0.2, petroleum ether/ethyl acetate=1:1. $^1H$ NMR (400 mHz, $CDCl_3$) δ 9.13 (s, 1H), 8.79 (s, 1H), 4.76 (s, 2H), 3.64 (s, 1H), 3.45 (s, 3H); The compound A5 (0.014 mmol) and phenyl azide (0.021 mmol, 1.5 eq) were dissolved in ethanol (8 mL), and copper sulfate (0.0021 mmol, 0.15 eq), sodium ascorbate (0.028 mmol, 0.2 eq), and aqueous solution (4 mL) of potassium carbonate (0.014, 1.0 eq) were added in a stirred way; the reaction system was stirred at room temperature for 24 hours; the system was then filtered through celite, extracted with DCM (3×50 mL), dried over anhydrous sodium sulfate, filtered to remove the drying agent, concentrated and subjected to column chromatography to obtain the target product compound 2. $^1H$ NMR (400 MHz, $CDCl_3$) δ 9.13 (s, 1H), 8.77 (s, 1H), 8.25 (s, 1H), 7.71 (d, J=7.6 z, 2H), 7.51 (t, J=7.2 Hz, 2H), 7.44 (d, J=7.2 Hz, 1H), 5.20 (s, 2H), 3.58 (s, 3H); $^{13}C$ NMR (151 MHz, $CDCl_3$) δ 166.2, 163.5, 144.0, 142.6, 136.9, 134.3, 133.7 (d, J=3.0 Hz), 130.0 (q, J=36.2 Hz), 129.9, 129.1, 126.7, 126.2 (d, J=3.0 Hz), 122.5 (q, J=273.3 Hz), 122.3, 120.7, 46.7, 37.1; HRMS (+ESI) m z calcd for $C_{19}H_{14}F_3N_6O_3S^+$ $[M+H]^+$=463.0795, found 463.0797.

Control 1

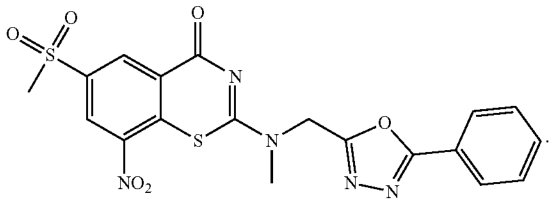

Control 2

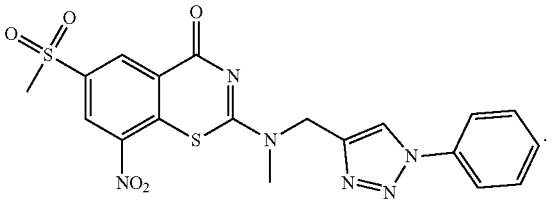

Example 3: Compound: 2-((((1-(4-fluorophenyl((1-1H-1,2,3-triazole-4-yl)methyl) (methyl) amino)-8-nitro-6-(trifluoromethyl)-4H-benzo [e] [1,3] Thiazin-4-ketone

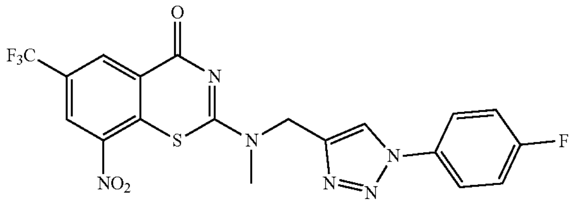 [SMILES: CN(Cc1cn(-c2ccc(F)cc2)nn1)c1nc(=O)c2cc(C(F)(F)F)cc([N+](=O)[O-])c2s1]

The operations were the same as that in Example 2, the azide was 4-fluorophenylazide, and the remainder was unchanged to obtain the compound 3 as a yellow solid (45 mg, yield: 65%). $^1$H NMR (400 MHz, $CDCl_3$) δ 9.12 (s, 1H), 8.77 (s, 1H), 8.27 (s, 1H), 7.70 (dd, J=7.6, 4.4 Hz, 2H), 7.20 (t, J=8.0 Hz, 2H), 5.18 (s, 2H), 3.57 (s, 3H). $^{13}$C NMR (151 MHz, $CDCl_3$) δ 166.2, 163.6, 162.7 (d, J=250.0 Hz), 144.0, 142.7, 134.3, 133.7 (d, J=2.4 Hz), 133.2, 130.0 (q, J=35.1 Hz), 126.6, 126.2 (d, J=3.0 Hz), 122.7 (d, J=8.4 Hz), 122.6, 122.5 (q, J=273.1 Hz), 116.9 (d, J=23.3 Hz), 46.7, 37.2. HRMS (+ESI) m/z calcd for $C_{19}H_{13}F_4N_6O_3S^+$ $[M+H]^+$=481.0700, found 481.0692.

Control 3

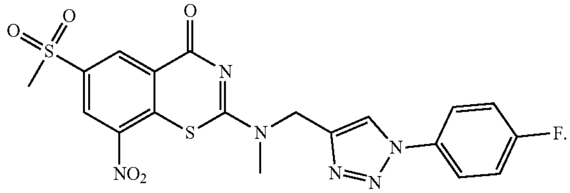

Example 4: Compound 4:2-((((5-(4-fluorophenyl-1,3,4-thiadiazole-2-yl)methyl) (methyl) amino)-8-nitro-6-(trifluoromethyl)-4H-benzo [e] [1,3] Thiazin-4-ketone

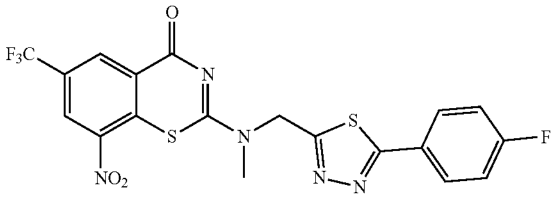 [SMILES: CN(Cc1nnc(-c2ccc(F)cc2)s1)c1nc(=O)c2cc(C(F)(F)F)cc([N+](=O)[O-])c2s1]

The operations were the same as that in Example 1, the side chain amine used was 1-(5-(4-fluorophenyl)-1,3, 4-thiadiazole-2-yl)-N-methylmethylamine to obtain the compound 6 (45 mg, yield: 50%) as a yellow solid. $^1$H NMR (400 MHz, $CDCl_3$) δ 9.17 (s, 1H), 8.81 (s, 1H), 8.02-7.87 (m, 2H), 7.15 (t, J=8.0 Hz, 2H), 5.43 (s, 2H), 3.54 (s, 3H); $^{13}$C NMR (151 MHz, $CDCl_3$) δ 170.0, 165.8, 164.7 (d, J=253.0 Hz), 164.0, 162.1, 144.1, 133.9 (d, J=3.0 Hz), 130.4, 130.2 (d, J=8.8 Hz), 129.9 (q, J=35.4 Hz), 126.6, 126.4 (d, J=3.2 Hz), 126.1, 122.4 (q, J=273.2 Hz), 116.6 (d, J=22.2 Hz), 49.8, 36.9; HRMS (+ESI) m/z calcd for $C_{19}H_{12}F_4N_5O_3S_2^+$ $[M+H]^+$=498.0312 found 498.0317.

Control 4

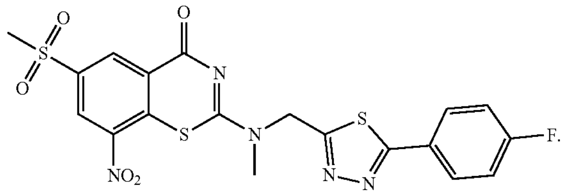

Example 5: Compound 5:2-(methyl((2-phenyloxazole-4-yl) methyl) amino)-8-nitro-6-(trifluoromethyl)-4H-benzo [e] [1,3] Thiazin-4-ketone

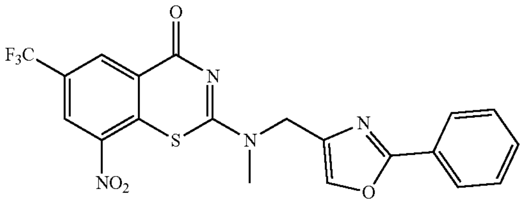 [SMILES: CN(Cc1coc(-c2ccccc2)n1)c1nc(=O)c2cc(C(F)(F)F)cc([N+](=O)[O-])c2s1]

The compound benzamide (2.00 mmol) was dissolved in ethanol:tetrahydrofuran (14 mL+7 mL=21 mL) (2:1), 1, 3-dichloroacetone (2.20 mmol, 1.1 equiv) was added with stirring, and reacted at 80° C. for 7 hours; then, the system was concentrated, extracted with ethyl acetate (20 mL×3), dried over anhydrous sodium sulfate, filtered, concentrated, and subjected to column chromatography (petroleum ether: ethyl acetate=15:1) to obtain an oily substance D1, $R_f$=0.3 (petroleum ether:ethyl acetate=15:1), yield: 90%.

The compound D1 (1.70 mmol) was dissolved in methanol (15 mL), methanol solution (5 mL) of methylamine was added under ice bath, and heated to room temperature for reaction for 5 hours; then, it was extracted with saturated sodium chloride (20 mL) and ethyl acetate (30 mL×5), dried over anhydrous sodium sulfate, filtered, concentrated, and subjected to column chromatography (dichloromethane: methanol=15:1) to obtain an oily N-methyl-1-(2-phenyloxazol-4-yl) methylamine (D2), $R_f$=0.3 (dichloromethane: methanol=15:1), yield: 93%; its operations were the same as that in Example 1, the side chain amine used was N-methyl-1-(2-phenyloxazol-4-yl) methylamine (D2) to obtain the compound 5 (45 mg, yield: 48%) as a yellow solid. $^1$H NMR (400 MHz, $CDCl_3$) δ 9.14 (s, 1H), 8.77 (s, 1H), 8.01 (br, 2H), 7.84 (s, 0.75H, major), 7.78 (s, 0.25H, minor), 7.46 (br, 3H), 5.05 (s, 1.5H, major), 4.87 (s, 0.5H, minor), 3.56 (s, 3H). HRMS (+ESI) m/z calcd for $C_{20}H_{12}F_3N_4O_4S^+$ $[M+H]^+$=463.0682 found 463.0683.

Control 5

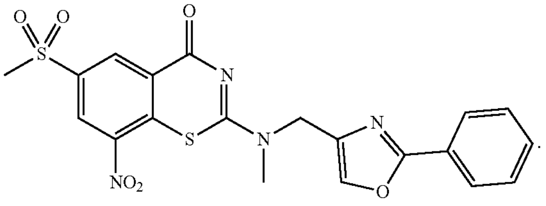

Determination of the activity of anti-*Mycobacterium tuberculosis*: The antimicrobial experiment adopted a microwell Alamar Blue fluorometric method, which is an existing conventional test method, and the experimental steps are briefly described as follows: 2 drops of 5% Tween 80 were dropped into a grinding flask, the cultured strain H37Rv (standard strain purchased from ATCC) was scraped and placed in the grinding flask; the grinding flask was tightened, and shaken for 5 minutes to separate bacteria; then it was set still for 20 min, before the physiological saline was added, and its turbidity was compared with the No. 1 turbidimetric tube to the same concentration, and the OD (OD=1 is $3.8\times10^8$, OD=0.2 is $1\times10^8$) of the bacteria liquid was measured to determine the concentration of the turbidimetric tube; it was diluted after turbidity comparison and conversion and mixed for standby; 100 μL of 7H9 mycobacteria culture medium and OADC enrichment medium were added into 1-11 wells of 96-well plate; 190 μL of 7H9+OADC was added into column 12 well; 10 μL of the prepared compound was added into the column 12 well of a 96-well plate added with the culture medium, and uniformly mixed; the pipette gun was adjusted to the scale of 100 μL to suck 100 μL of mixed liquor from the column 12 well to be added to the column 11 well to be mixed together to suck 100 μL of mixed liquor from the column 11 well to be added to the column 10 well, and the like until the column 2 well, and the last 100 μL of mixed liquor was discarded and not added to the column 1 well (control well); 100 μL of standby bacterial solution was sucked to be added to the 96-well plate and the gun head shall not touch the solution in the well; the 96-well plate was placed carefully in an incubator at 37° C. for 8 days for culturing; the solution of 5% Tween 80:alamar blue=5:2 was prepared and the 96-well plate was taken out, and 70 uL of the prepared solution was added into each well and placed in the incubator at 37° C. for 2 days for culturing. MIC value was checked; existing PBTZ169 and isoniazid were used as positive controls.

The human liver microsome metabolism half-life period test method comprises the following steps: the concentration of the compound was 1.0 μM (DMSO), the concentration of human liver microsomes was 0.5 mg/mL, the cells were incubated at 37° C. in PBS buffer at pH 7.4, 1.0 mM, samples were taken at 0, 5, 15, 30, and 45 minutes, and the concentration of the drug was quantified by LC/MS analysis.

Solubility test: In phosphate buffer saline solution (45 mM $KH_2PO_4$, 45 mM KOAc, 75 mM KCl, 45 mM ethanolamine, pH 7.4) with a total volume of 1000 μL was add DMSO mother solution of the compound to be tested (the final concentration of DMSO was lower than 1%). The solubility of the compounds was tested. 10 μL of different concentrations of compound DMSO mother solution was mixed with 990 μL of buffer solution in a 1.5 mL centrifuge tube and shaken at room temperature for 4 hours. It was filter with a membrane filter with a pore size of 0.3 μm. The filtrate was quantitatively analyzed by HPLC.

The minimal inhibitory concentration MIC (ng/mL) of the above compounds against *Mycobacterium tuberculosis* (H37 Rv, standard tuberculosis strain), metabolic half-life period in human liver microsomes ($T_{1/2}$, min) and solubility (g/mL) were as follows:

| | MIC | $T_{1/2}$ | Solubility | | MIC | $T_{1/2}$ | Solubility |
|---|---|---|---|---|---|---|---|
| Example 1 | 3 | 68.22 | 0.15 | Example 3 | 4 | 115.5 | 0.12 |
| Control 1 | 14 | 45.93 | Not tested | Control 3 | 15 | 27.61 | Not tested |
| Example 2 | 4 | 100.43 | 0.13 | Example 4 | 16 | 34.3 | Not tested |
| Control 2 | 22 | 53.7 | Not tested | Control 4 | 24 | 13.19 | Not tested |
| Example 5 | 3 | 33.62 | 0.11 | PBTZ169 | 1.83 | 38 | <0.01 |
| Control 5 | 15 | 21.03 | Not tested | isoniazid INH | 28 | Not tested | Not tested |

The results show that: the compound of the invention showed obvious bacteriostatic effect which is far superior to that of positive control isoniazid. Compared with positive control PBTZ169, the compound of the invention has obviously good metabolic half-life period in human liver microsomes ($T_{1/2}$, min) and water solubility, which shows that it has good in vivo stability and better water solubility.

The invention claimed is:

1. A 6-trifluoromethyl-substituted benzothiazinone derivative selected from the group consisting of:

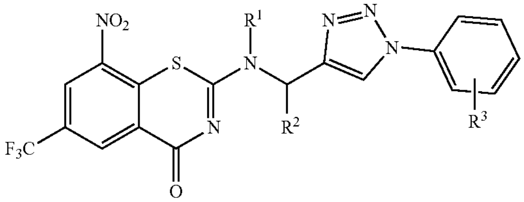

,

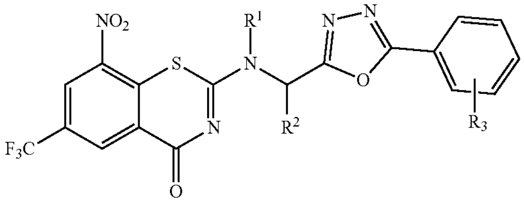

,

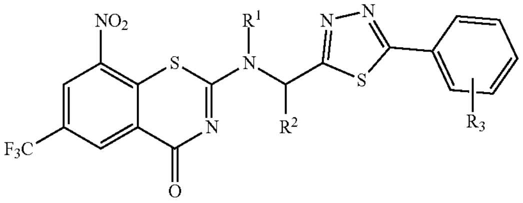

and

-continued

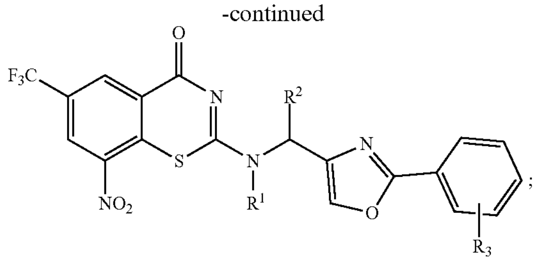

wherein: $R^1$ is hydrogen, methyl or ethyl; $R^2$ is hydrogen, methyl or ethyl; and $R^3$ is hydrogen or halogen.

2. The 6-trifluoromethyl-substituted benzothiazinone derivative according to claim 1, selected from the group consisting of:

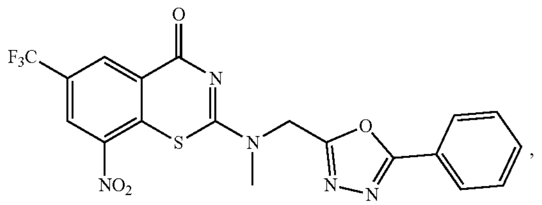

,

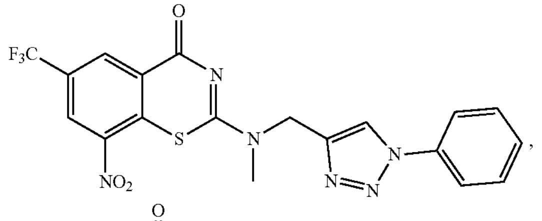

,

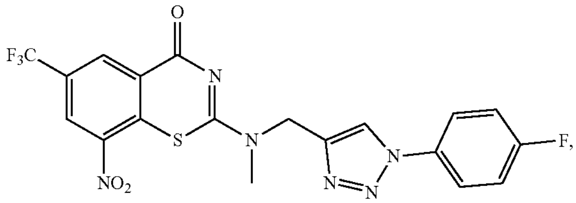

,

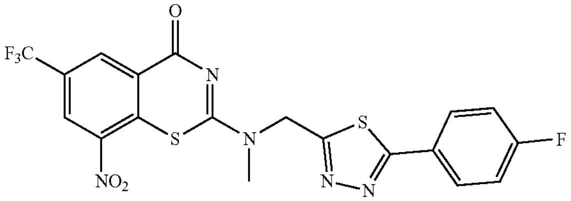

and

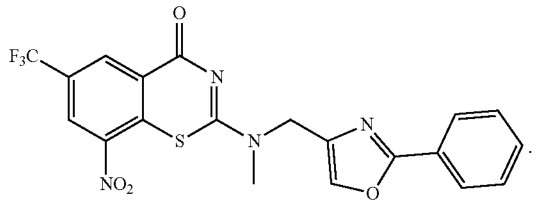

.

3. A method of inhibiting tubercle bacillus in a subject, comprising:

administering to said subject a 6-trifluoromethyl-substituted benzothiazinone derivative according to claim 1.

4. A pharmaceutical composition comprising the 6-trifluoromethyl-substituted-benzothiazinone derivative according to claim 1 as an active ingredient.

5. A method of preparing the 6-trifluoromethyl-substituted benzothiazinone derivative according to claim 1, comprising: reacting a compound A5,

A5

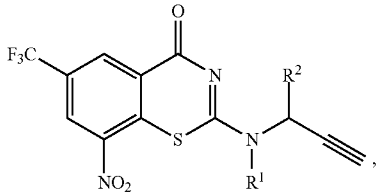

, with an azide compound,

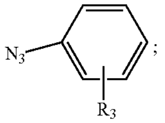

;

or reacting a compound A4,

A4

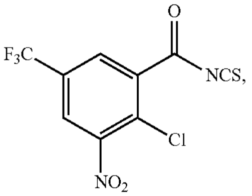

with a compound BC,

BC

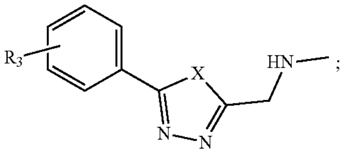

;

or reacting the compound A4,

A4

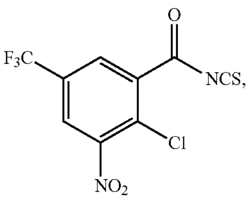

with a compound D2,

D2

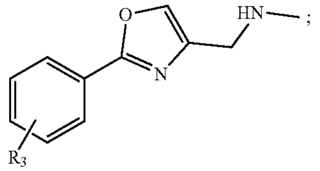

wherein: $R^1$ is hydrogen, methyl or ethyl; $R^2$ is hydrogen, methyl or ethyl; and R3 is hydrogen or halogen; X is O or S.

6. The method according to claim 5, wherein the reaction of the compound A5 and the azide compound is carried out at room temperature in the presence of a copper salt, a reducing agent and inorganic base; the reaction of compound A4 with the compound BC is carried out at room temperature; the reaction of compound A4 with compound D2 is carried out at room temperature.

7. The method according to claim 5, wherein the compound A4 is prepared by a process comprising: reacting compound A1,

A1

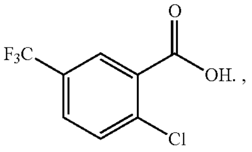

with oxalyl chloride.

* * * * *